US010639288B2

(12) United States Patent
Tamura et al.

(10) Patent No.: US 10,639,288 B2
(45) Date of Patent: May 5, 2020

(54) ANTI-AGING SKIN CARE COMPOSITIONS AND REGIMENS

(71) Applicant: The Procter & Gamble Company, Cincinnati, OH (US)

(72) Inventors: Makio Tamura, Cincinnati, OH (US); Rosemarie Osborne, Oxford, OH (US); Heather Lynn Rocchetta, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 605 days.

(21) Appl. No.: 14/851,418

(22) Filed: Sep. 11, 2015

(65) Prior Publication Data

US 2016/0074301 A1 Mar. 17, 2016

Related U.S. Application Data

(60) Provisional application No. 62/049,972, filed on Sep. 12, 2014.

(51) Int. Cl.
| | |
|---|---|
| *A61K 31/202* | (2006.01) |
| *A61K 8/67* | (2006.01) |
| *A61K 8/97* | (2017.01) |
| *A61K 8/64* | (2006.01) |
| *A61K 8/06* | (2006.01) |
| *A61K 49/00* | (2006.01) |
| *A61Q 19/08* | (2006.01) |
| *A61K 8/31* | (2006.01) |
| *A61K 8/34* | (2006.01) |
| *A61K 8/368* | (2006.01) |
| *A61K 8/37* | (2006.01) |
| *A61K 8/58* | (2006.01) |
| *A23L 33/12* | (2016.01) |
| *A23L 33/00* | (2016.01) |
| *A23L 29/10* | (2016.01) |
| *A61K 9/00* | (2006.01) |
| *A61K 9/107* | (2006.01) |
| *A61K 35/60* | (2006.01) |

(52) U.S. Cl.
CPC ............ *A61K 31/202* (2013.01); *A23L 29/10* (2016.08); *A23L 33/12* (2016.08); *A23L 33/30* (2016.08); *A23L 33/40* (2016.08); *A61K 8/062* (2013.01); *A61K 8/31* (2013.01); *A61K 8/342* (2013.01); *A61K 8/345* (2013.01); *A61K 8/368* (2013.01); *A61K 8/37* (2013.01); *A61K 8/585* (2013.01); *A61K 8/64* (2013.01); *A61K 8/67* (2013.01); *A61K 8/97* (2013.01); *A61K 9/0029* (2013.01); *A61K 9/107* (2013.01); *A61K 35/60* (2013.01); *A61K 49/0006* (2013.01); *A61Q 19/08* (2013.01); *A23V 2002/00* (2013.01); *A61K 2800/20* (2013.01); *A61K 2800/48* (2013.01); *A61K 2800/884* (2013.01)

(58) Field of Classification Search
None
See application file for complete search history.

(56) References Cited

U.S. PATENT DOCUMENTS

| | | |
|---|---|---|
| 5,997,890 A | 12/1999 | Sine |
| 6,492,326 B1 | 12/2002 | Bissett |
| 6,696,049 B2 | 2/2004 | Vatter |
| 2008/0206373 A1 | 8/2008 | Millikin |
| 2012/0034613 A1 | 2/2012 | Gopaul |
| 2013/0337087 A1 | 12/2013 | Finlay |
| 2014/0163118 A1* | 6/2014 | Giuliani ............ G01N 33/5088 514/789 |

FOREIGN PATENT DOCUMENTS

| | | |
|---|---|---|
| FR | 2 947 727 A1 | 8/2011 |
| WO | WO2012151346 | 11/2012 |

OTHER PUBLICATIONS

U.S. Appl. No. 14/853,051, filed Sep. 14, 2015, Makio Tamura.
Farris, P. et al. "A High-Potency, Multimechanism Skin Care Regimen Provides Significant Antiaging Effects: Results From a Double-Blind, Vehicle-Controlled Clinical Trial" *J Drugs Dermatol.* 2012; 11(12):1447-1454.
Langerfelder "Eigengene networks for studying relationships between co-expression modules", *BMC Systems Biology* 2007, 1-54.
Finlay, et al. "Skin Biomarkers Confirm the Anti-Oxidant Activity of Olive Derivatives and Yeast Ferment Filtrate", P&G 67th Annual Meeting of American Academy of Dermatology (2009).
Bissett el al. "Niacinamide: A B Vitamin that Improves Aging Facial Skin Appearance" Dermatologic Surgery; 2005; 31:860-865.
Draelos, Z. "Clinical Situations Conducive to Proactive Skin Health and Anti-Aging Improvement" The Society for Investigative Dermatology 2008; 4 pages.
Osborne, R. et al. "In Vitro Biomarker Responses to a New Anti-Aging Peptide, PAL-KT", American Academy of Dermatology 67th Annual Meeting Media Resources, 2009.

(Continued)

*Primary Examiner* — Jake M Vu
(74) *Attorney, Agent, or Firm* — John G. Powell

(57) ABSTRACT

Multi-step cosmetic regimens are provided to improve the appearance of aging skin. A target portion of skin that exhibits a sign of skin aging is identified. A first formulation is topically applied, comprising at least one active possessing an ability to transcriptionally up-regulate an eigengene derived from a genetic co-expression module for one or more biological themes associated with skin cleansing and/or skin detoxification, and/or skin hydration to the target portion of skin. A second formulation is also topically applied, comprising at least one active possessing an ability to transcriptionally up-regulate an eigengene derived from a co-expression module for one or more biological themes associated with skin repair and/or rebuilding to the target portion of skin.

2 Claims, 14 Drawing Sheets

(56) References Cited

OTHER PUBLICATIONS

International Search Report PCT/US2015/049604; dated Dec. 9, 2015; 14 pages.
Fu, J.J. et al: "A randomized controlled comparative study of the wrinkle reduction benefits of a cosmetic niacinamide/peptide/retinyl propionate product regimen vs. a prescription 0.02% tretinoin product regimen", British Journal of Dermatology, vol. 162, No. 3, Mar. 1, 2010 (Mar. 1, 2010), pp. 647-654.
GNPD [Online] MINTEL; Aug. 2012 (Aug. 2012), "Regimen Kit", Database accession No. 1856447.
GNPD [Online] MINTEL;Jun. 2009 (Jun. 2009), "Facial Kit", Database accession No. 1101942.
GNPD [Online] MINTEL;May 2009 (May 2009), "Pomfacial Kit", Database accession No. 1092292.
GNPD [Online] MINTEL;"Skin Tightening Serum", Sep. 2010; Database accession No. 1406349.
International Search Report PCT/US2015/049937; dated Dec. 9, 2015.
Gopaul, R.. "Salicin regulates the expression of functional 'youth gene clusters' to reflect a more youthful gene expression profile" International J Cosmetic Science (2011), 33, 416-420.
Chang, "Identification of Genes Promoting Skin Youthfulness by Genome-Wide Association Study" J. Investigative Dermatology (2014), vol. 134, pp. 651-657.

\* cited by examiner

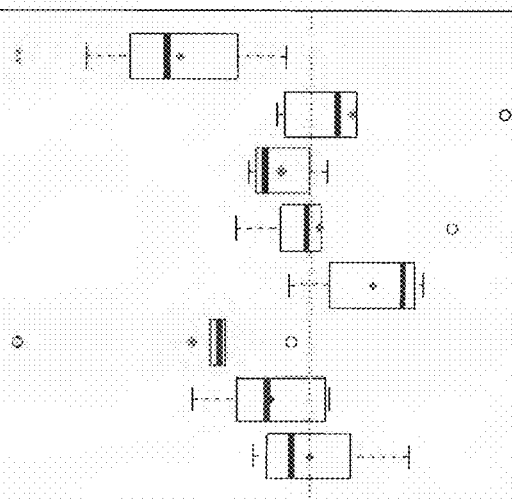
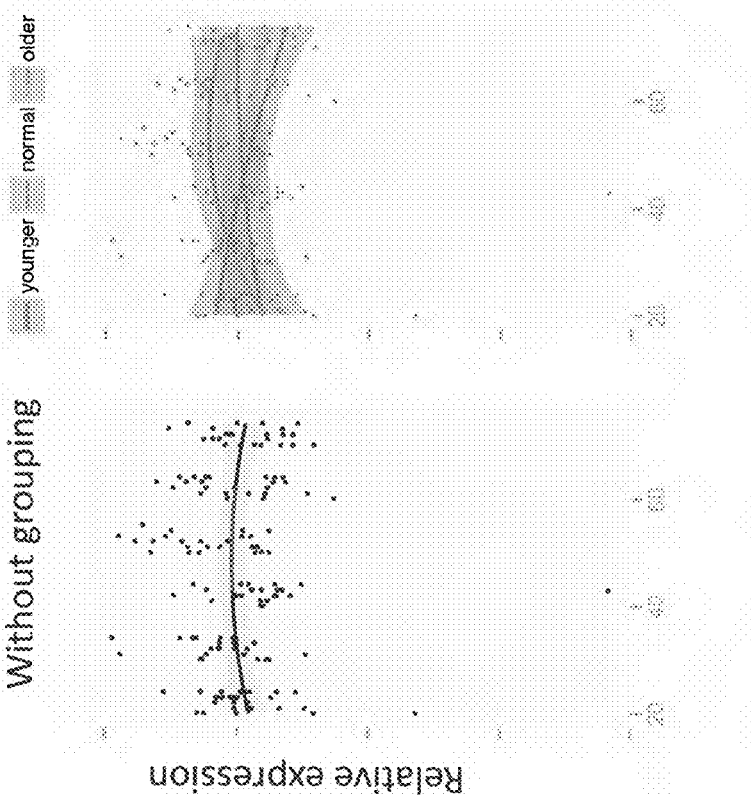
Figure 1B
Younger Looking Genes in Total Dermis (243 Genes)
Expression change of the first Eigengene consisting of the younger looking genes from dermis face (representing 19% of total variance)
Treatment effect of formulation actives on the first Eigengene
* p.val < .001,  p.val < .01, * p.val < .05

Figure 2

26 Biological Themes implicated by "Younger-appearance" gene set

Table 1
Clean & Detox Biological Themes

Induction of apoptosis
Protein catabolic process
Regulation of autophagy
Regulation of endopeptidase activity
Regulation of proteolysis Table 2
Repair & Rebuild Biological Themes Amino sugar biosynthetic process
Cell adhesion_junction
Cell growth
Cytoskeleton organization
DNA repair
Glycerolipid metabolic process
Response to growth factor stimulus
RNA processing
Wnt receptor signaling pathway Table 3
Nondiscriminant Biological Themes Adaptive immune response
Cellular macromolecule localization
Defence response
Innate immune response
Nitrogen compound transport
Nucleoside catabolic process
Phosphatidylinositol-mediated signaling
Protein acetylation
Regulation of developmental growth
Regulation of kinase activity
Response to cytokine stimulus
Response to hormone stimulus

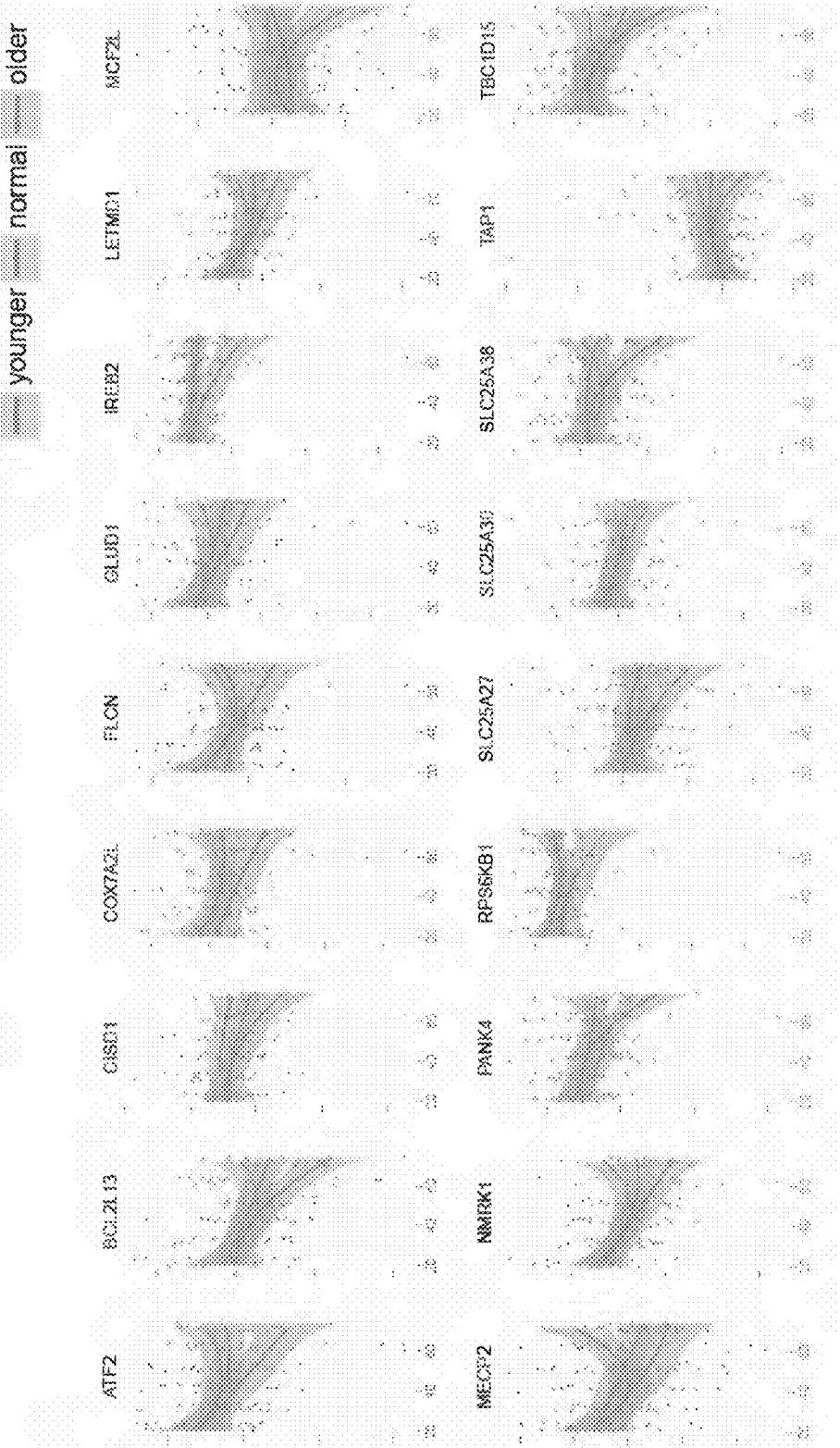

Figure 6A

Younger Looking Genes Relating Skin Barrier
40 Genes

| | | |
|---|---|---|
| ADD3 | INADL | POU3F1 |
| APC | IQGAP1 | PSEN1 |
| ATP2C1 | LAMA5 | PTPRJ |
| CDH1 | LIG4 | PVRL3 |
| CERS3 | LIMD1 | RAC1 |
| CTNND1 | LRP4 | RAP1B |
| DSC3 | MAGI1 | RUNX3 |
| ERBB2IP | NOTCH1 | SATB1 |
| EVL | PDPK1 | SAV1 |
| FGFR3 | PDZD2 | SMAD4 |
| FRMD4A | PKD1 | TMEM204 |
| FZD6 | PKN2 | VANGL2 |
| GAB1 | PNN | WNT10B |
| GAB1 | | |

These genes are involved in

- anchoring junction
- adherens junction
- cell-cell adherens junction
- desmosome
- gap junction
- cell-cell junction
- cell-substrate junction
- hemidesmosome
- skin development

Figure 7A

Younger Looking and Known Age Associated 27 Genes

ANG
ATF2
ATM
CCL25
CDKN2B
CREB1
CREBBP
ERCC5
IL6ST
JAK2
KAT6A
MORC3
MXI1
NR3C1

PDGFB
PDGFRA
PDPK1
PIK3CA
PSEN1
RAD52
RB1
S100B
SIRT1
SUMO1
TAF1
TBP
TP73

Over-Represented Theme among these genes are

- Transcription factor binding - CREBBP,TBP,CREB1,NR3C1,SUMO1,TP73,TAF1,KAT6A,RB1

- Transcription, DNA-dependent - CREB1,SIRT1,NR3C1,TP73,RB1,ATF2,KAT6A,CDKN2B,TAF1,MXI1,CREBBP,TBP,PDPK1

- Response to DNA damage stimulus - RAD52,PSEN1,SIRT1,ATM,TP73,TAF1,ERCC5

Heat Map of Anti-Aging Effect of Exemplary formulation actives

ANTI-AGING SKIN CARE COMPOSITIONS AND REGIMENS

TECHNICAL FIELD

The subject matter of the disclosure relates to multi-step cosmetic regimens and topical skin care compositions specifically formulated according to gene expression network studies to provide enhanced anti-aging benefit when used by a consumer according to a particular regimen.

BACKGROUND

The skin is a complex and dynamic organ that provides a highly regulated interface between the external and internal environment. Skin aging is a multi-factorial process and proceeds as a function of both intrinsic stressors such as free-radical generation from metabolic and catabolic processes, and extrinsic stressors such as chemical and UV-light exposure and generation of free radicals at the surface, as well as from genetic determinism. Wrinkles, loss of tone and firmness, a decrease in moisture retention capacity, and development of pigment irregularities, are all well-known age-related effects that underpin an appearance of "aged skin."

Given the significant impact that skin aging can have on one's appearance and self esteem, there is an ongoing effort to identify cosmetic agents and develop formulations that are effective at treating or improving the appearance of aging skin. Scientists have established that skin aging results from multiple biological mechanisms, and that countering or reversing the effects of aging must be addressed by a multi-mechanistic approach. Hence, over the past several decades the focus has been on formulating skin anti-aging compositions based on identifying the underlying processes implicated in the appearance of aging skin, and developing or identifying skin care agents that specifically counter or shift the equilibrium in these processes toward a more youthful appearance.

An early approach to cosmetic product development reflecting the multi-mechanistic paradigm was to formulate a single composition with several skin-care actives identified as effective for different or multiple mechanisms. Application regimens generally involved multiple applications of the same formulation across a dosing or treatment time frame. Another early product development approach was simply to add identified actives to existing delivery products in order to piggyback off existing consumer habits, such as routine application of morning moisturizers and night eye-creams. Many cosmetic products are now available to consumers that have been formulated with multiple anti-aging skin care agents; however interaction of biological processes activated by agents in the same formulation or between formulations in accordance with any particular application regimen was not scientifically investigated.

Recently, scientists at Tulane University demonstrated anti-aging efficacy in a regimen involving daily application of multiple compositions, each composition formulated to deliver certain actives at times theoretically linked with an optimal benefit effect. The study investigated the impact of application of four different product formulations, a cleanser, day-cream, night-cream, and eye-cream on a daily basis. Each product was known and contained actives with established mechanistic-based benefits, and each product was already marketed as having a daily preferred time for application. In the experimental protocol, control subjects were provided formulations comprising the same delivery vehicles and excipients, including sun screen, without the actives (*J Drugs Dermatol.* 2012; 11(12):1447-1454) and all subjects were instructed to follow a regimen comprising application of each formulation at a specific time of day for up to 30 weeks. This study, however, failed to consider or control for any effect specifically due to the regimen. Both experimental and control subjects followed the same application regimen, and there was no control population enabling comparison of order of application of specific actives and/or for investigation of any differential effect on target benefit that may have been conferred (or compromised) by order of application. Further, although the study noted the theoretical bio-mechanistic basis for inclusion of the eight active ingredients in the four compositions, there was no scientific foundation based on interplay between or among the mechanisms suggested or confirmed as a basis for an application regimen and in particular from the order of application of the actives.

Skin care regimens suggesting use of an exfoliating agent along with surfactants/soaps in a skin cleansing formulation prior to application of anti-aging formulations are also known in the art. However, known cleansing formulations suffer from the lack of scientific insight/foresight or basis with respect to what actives or mechanistic manipulations/effects in addition to cleansing might provide additional priming of the skin for receptivity to subsequently delivered actives present in a second formulation. Most particularly, formulation of compositions as part of specific multi-step regimens based on interaction between actives and the biological processes/mechanisms they regulate/activate have not been considered. In part this was due to difficulty in perceiving the more subtle interactions and variances among cosmetic agents and the processes they regulate.

More recently, however, cosmetic investigators have been able to validate biological process regulation by cosmetic actives through gene transcriptional studies. The principles of genetics and transcriptional regulation have been applied to designing and validating skin anti-aging formulations. Generally, these studies were based on global micro-array analyses of treated skin versus untreated skin and identification of genes differentially regulated in response to the treatment. In even more refined studies including studies by some of the present investigators, methods and formulations based on identification and categorization of skin care agents according to ability to transcriptionally regulate genes implicated in specific biological pathways known to be associated with skin health and functioning were developed and/or validated (see, e.g., application Ser. No. 13/022,191). However, although active synergies were sometimes be observed, mechanistic interaction between actives and interplay between the implicated biological processes when actives are co-formulated or applied in tandem or according to specific application regimens were not considered.

Surprisingly, by application of recently developed principles of bioinformatics that refine the genetic model, it has now been found that order of application of specific skincare actives can be manipulated to achieve an enhanced anti-aging benefit over random or reverse application of the same actives across a daily dosing treatment time frame protocol.

Under the current model, genes and gene expression products may be grouped according to biological pathways, processes or "themes" in which expression regulation by an active is implicated. According to a relatively new bioinformatics-generated genetic model, "eigengenes" may be derived to elucidate relationships between the pathways (Langerfelder and Hovarth, *BMC Systems Biology* 2007, 1:54, 1752-0509). Under the Eigengene model, a "module" is a group of interconnected genes that forms a biological pathway, process or theme, and an intersecting set of two or more modules is called a "co-expression module." A gene expression profile of a module or co-expression module may be represented by an "eigengene," and eigengene networks may be constructed to represent the relationships between and within genetic co-expression modules. Derivation of an "eigengene" collapses many data points into a single vector. An eigengene may be thought of as a summary of a module expression profile into a single representative gene. An eigengene reflects the variance between the genes comprising the modules.

The present investigators posited that even the subtle impact of interactions between biological processes triggered by cosmetic actives may be studied by applying these principles to investigation of cosmetic anti-aging formulations and regimens. Surprisingly, it was discovered that order of topical application of skin care compositions comprising anti-aging actives makes a difference in the efficacy of the overall treatment benefit, and that formulations may be developed to maximize the effect of regimen on the anti-aging benefit.

SUMMARY

Accordingly the present invention provides cosmetic anti-aging formulations and regimens scientifically designed to provide anti-aging actives in a time frame that optimizes a desired anti-aging benefit. In particular, a regimen comprising application of a composition formulated to provide cleansing, detoxifying and hydrating effects prior to application of a composition formulated to provide repairing and rebuilding effects yields an enhanced anti-aging end-target result.

Embodiments of the invention provide a multi-step cosmetic regimens effective for improving the appearance of aging human skin. A regimen comprises: (a) identifying a target portion of skin that exhibits a sign of skin aging; (b) topically applying a first formulation comprising at least one active possessing an ability to transcriptionally up-regulate an eigengene derived from a genetic co-expression module for one or more biological themes associated with skin cleansing and/or skin detoxification, and/or skin hydration to the target portion of skin, and (c) topically applying a second formulation comprising at least one active possessing an ability to transcriptionally up-regulate an eigengene derived from a co-expression module for one or more biological themes associated with skin repair and/or rebuilding to the target portion of skin, wherein application of (c) follows application of (b).

Other embodiments are directed to cosmetic skin treatment kits comprising a first skin care composition and a second skin care composition separately contained. The first composition is formulated to comprise at least one active possessing an ability to transcriptionally up-regulate an eigengene derived from a genetic co-expression module for one or more biological themes associated with skin cleansing and/or skin detoxification and/or skin hydration to the target portion of skin. The second composition is formulated to comprise at least one active possessing an ability to transcriptionally up-regulate an eigengene derived from a co-expression module for one or more biological themes associated with skin repair and/or rebuilding, instructions to apply the first composition to a target area of skin prior to applying the second composition to the target area of skin. The kit may optionally comprise at least one applicator to effectuate topical application of the first and/or the second skin care composition to the target area of skin, or the containers may be designed for application directly to the target area, or to fingers of the consumer for applying directly to a target area.

A broad embodiment provides analogous methods for providing other cosmetic benefits to human skin by identifying agents effective for transcriptionally up-regulating an eigengene derived from a genetic co-expression module for one or more biological themes associated with a desirable cosmetic phenotypic of human skin. Methods comprise: deriving an eigengene for a co-expression module determined from a set of genes transcriptionally up-regulated in human skin exhibiting the desirable cosmetic phenotypic and a set of genes associated with the one or more biological themes; treating skin with a putative agent; conducting a transcriptional assessment of the eigengene in the treated skin; and identifying the putative agent as an effective agent if the eigengene is up-regulated in the treated skin.

Eigengenes and related probe-sets useful as biomarkers or standards for cosmetic conditions and effects are also provided. In one embodiment an eigengene is derived from a co-expression module of a first set of genes differentially expressed in a desired cosmetic phenotype and a second set of genes implicated in a biological pathway over-represented in the first set of genes.

These and other embodiments will be more fully understood by reference to the Figures and Detailed description below, although it should be noted that Figures and Examples are for illustrative purposes and should not be construed as limiting the full scope of the subject matter as defined by the claims appended hereto. All references (e.g., printed publications such as books, papers, patents, patent applications, catalogs, databases) are incorporated herein by reference. In the event of a conflict or inconsistency, the present specification, as modified by any amendments thereto, shall control.

BRIEF DESCRIPTION OF THE FIGURES

FIGS. 1A and 1B. 1A. Graph of age versus expression for Eigengene representing "younger-appearance" module and chart showing effects of exemplary actives on Eigengen. Younger-appearance genes in total epidermis; 1B. Younger-appearance genes in total dermis.

FIG. 2. 26 biological themes over-represented in "younger-appearance" module divided into cosmetic effect categories.

FIGS. 5A and 5B. 5A. Graph of Eigengene of co-expression module for "younger-appearance" and "Energy-related" and chart showing effects of exemplary actives on Eigengene; 5B. Graph of individual co-expression module genes as a function of age.

FIGS. 6A and 6B. 6A. List of genes in co-expression module for "younger-appearance" and "skin barrier"; 6B. Graph of Eigengene of co-expression module for "younger-appearance" and "skin barrier" and chart showing effects of exemplary actives on Eigengene.

FIGS. 7A and 7B. 7A. List of genes in co-expression module for "younger-appearance" and "age-associated"; 7B. Graph of Eigengene of co-expression module for "younger-appearance" and "age-associated" and chart showing effects of exemplary actives on Eigengene.

DETAILED DESCRIPTION

Figure 1A:
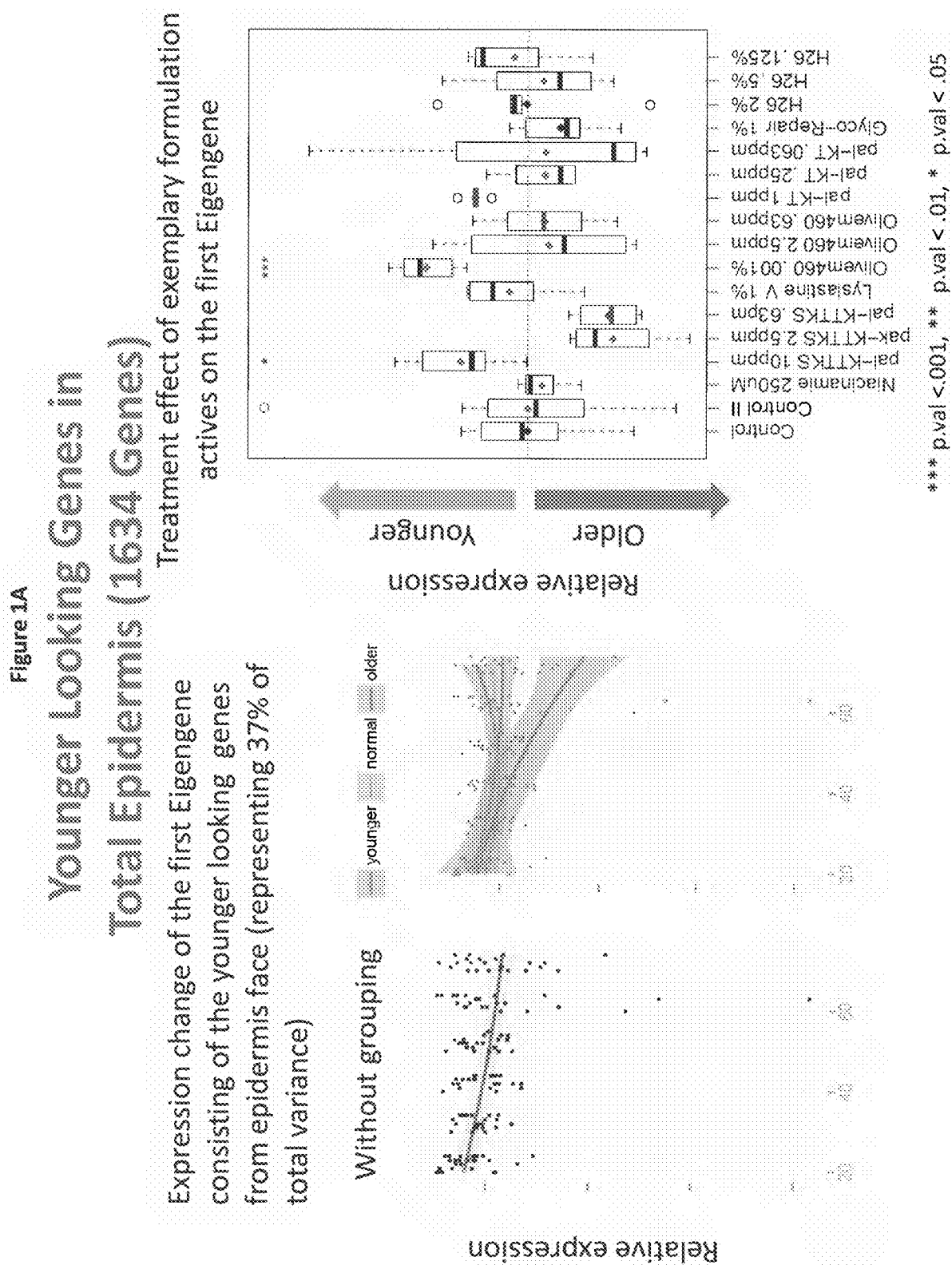

While the specification concludes with the claims particularly pointing out and distinctly claiming the invention, it is believed that the present invention will be better understood from the following description.

All percentages and ratios used herein are by weight of the total composition and all measurements made are at 25° C., unless otherwise designated. All ranges recited herein are inclusive and combinable; therefore, every range given throughout this specification will include every narrower range that falls within such broader range as if such narrower ranges were all expressly written herein. The number of significant digits conveys neither a limitation on the indicated amounts nor on the accuracy of the measurements. All measurements are understood to be made at ambient conditions. All such weights as they pertain to listed ingredients are based on the active level and do not include carriers or by-products that may be included in commercially available materials, unless otherwise specified.

The compositions of the present invention can comprise, consist essentially of, or consist of, the essential components as well as optional ingredients described herein. As used herein, "consisting essentially of means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

"Apply" or "application," when referring to a composition, means to topically apply or spread the composition onto a human skin surface such as the epidermis.

"Dermatologically acceptable" means that a composition or components described are suitable for use in contact with human skin tissue without undue toxicity, incompatibility, instability, allergic response, and the like.

"Effective amount" means an amount of a compound or composition sufficient to significantly induce a positive appearance and/or feel benefit, but low enough to avoid serious side effects (i.e., to provide a reasonable benefit to risk ratio, within the scope of sound judgment of the ordinary skilled artisan). For example, an effective amount of pal-KT and carob fruit extract herein means an amount of the two materials in combination that is sufficient to significantly induce a positive appearance and/or feel benefit, but low enough to avoid serious side effects (i.e., to provide a reasonable benefit to risk ratio, within the scope of sound judgment of the skilled artisan). The amount of an extract that is "effective" can differ from one particular source (e.g., manufacturer) of extract to another, and can be determined by the skilled artisan based upon the particular extract product's level of activity (e.g., level of active components present). As with any extract, the concentration of active components in the particular extract product to be used will depend on factors such as the final dilution volume of the extract product, the particular extraction method employed, the natural range of variation among individual plants, and other common factors known to those skilled in the art.

"Facial skin surface" means one or more of forehead, periorbital, cheek, perioral, chin, and nose skin surfaces.

"Skin care actives," or "actives," means compounds that, when applied to the skin, provide a benefit or improvement to the skin.

"Improving the appearance of aging skin" or "improving the texture of aging skin" means effecting a visually and/or tactilely perceptible positive change, or benefit, in skin texture appearance and/or feel. These terms also include preventing or delaying the appearance of one or more textural signs of skin aging. Benefits that may be provided include, but are not limited to, one or more of the following: improving the appearance of wrinkles, fine lines, coarse deep lines, crevices, bumps; preventing loss of skin elasticity, for example, due to loss, damage and/or inactivation of functional skin elastin, resulting in such conditions as elastosis, sagging, loss of skin recoil from deformation; and combinations thereof. Improving the appearance of aging skin may also be viewed as decreasing magnitude of a negative discordance between chronological age and apparent age, and preserving or increasing magnitude of a positive discordance between chronological age and apparent age. Negative discordance exists where chronological age is less than apparent age and positive discordance exists where chronological age is greater than apparent age. Positive discordance in the top 30% of women is referred to herein as "successful aging."

"Textural signs of skin aging" include but are not limited to, all outward visibly and tactilely perceptible skin texture manifestations, as well as any macro- or microeffects, due to undesired changes in skin texture due to aging. These signs may result from processes which include, but are not limited to, the development of textural discontinuities such as wrinkles and coarse deep wrinkles, fine lines, skin lines, crevices, bumps, unevenness or roughness; loss of skin elasticity; keratoses; abnormal differentiation; hyperkeratinization; elastosis; collagen breakdown, and other histological changes in the stratum corneum, dermis, or epidermis; and combinations thereof.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

As used herein, a subject's chronological age is the subject's age measured conventionally in years since birth. A subject's apparent age is the subject's age relative to other subjects determined from a comparative assessment protocol. A subject exhibits positive age discordance if the subject's apparent age is younger than the subject's chronological age, and a subject exhibits negative age discordance if the subject's apparent age is greater than the subject's chronological age.

The present investigators have surprisingly found that order of application of topical skin care compositions comprising actives selected according to which biological process/pathway is activated, makes a difference in the over-all efficacy of anti-aging treatments. In particular, a regimen comprising application of a composition formulated with actives associated with biological processes relating to cleansing, hydrating and detoxifying skin prior to application of a composition formulated with actives associated with biological processes relating to repairing and rebuilding skin provides superior end-target results when compared to regimens comprising (1) application of a single composition comprising the same actives and (2) application of the same compositions in reverse order.

The science of bioinformatics, which enables detection of subtle effects by utilizing data compression techniques, has been applied for the first time to formulation of cosmetic compositions for very specific biological effect. It is known that genes and gene expression products may be grouped according to biological pathways, processes or "themes" in which expression is implicated. In the bioinformatics model of gene network theory, these groupings are called "modules." An intersecting set of two or more modules is called a "co-expression module." The gene expression profile (transcriptomic profile) of a module or co-expression module may be represented by an "eigengene," and eigengene networks may be constructed to elucidate the relationships between co-expression modules.

Gene co-expression networks may be constructed from gene expression microarray data to provide information on the relationships between transcripts. A "module" is a group of interconnected genes that forms a biological pathway, process or theme. A co-expression module represents a higher-order organization. Derivation of an "eigengene" captures many data points into a single vector. An eigengene may be thought of as a summary of a co-module profile into a single representative gene. Because an eigengene is derived from a very select set of genes and accounts for variances among subjects, perturbations which may go unnoticed in an entire transcription profile may prove salient in effect on the eigengene.

A first module comprising a set of genes differentially expressed by "younger appearing" skin defined according to a protocol set forth in Example 1, is generated. Analysis of the set reveals over-represented biological themes. The intersection of "younger appearance" module with modules generated from sets of genes associated with specific over-represented biological processes or related groups of over-represented biological processes provides co-expression modules comprising the genes of each pathway specifically implicated in achieving "younger appearing" skin. An eigengene is then derived for each co-expression module of interest and actives may be tested for impact on the eigengene.

One embodiment of the invention provides a multi-step regimen effective for improving the appearance of aging human skin. The regimen comprises (a) identifying a target portion of skin that exhibits a sign of skin aging; (b) topically applying a first formulation comprising at least one active possessing an ability to transcriptionally up-regulate an eigengene derived from a genetic co-expression module for one or more biological themes associated with skin cleansing and/or skin detoxification, and/or skin hydration to the target portion of skin, and (c) topically applying a second formulation comprising at least one active possessing an ability to transcriptionally up-regulate an eigengene derived from a co-expression module for one or more biological themes associated with skin repair and/or rebuilding to the target portion of skin, wherein application of (c) follows application of (b). In specific embodiments the regimen includes step (a) followed by more than one step (b) applications. In very specific embodiments the regimen is a two-application step regimen. In some embodiments the regimen includes rinsing between step (a) and step (b).

The regimen is performed on a dosing schedule varying from once daily to twice daily and up to 4 times daily if re-application is desired, for example, after swimming or excessive sweating. Treatment time frames range from one week to one month to one year or of an indeterminate length of time defined by the cosmetic consumer. According to a very specific embodiment, the dosing schedule is at least one day dosed across a time frame of at least one week.

In most cases the regimen should be practiced such that application of (c) follows the application of (b) substantially immediately. In some embodiments a time gap between applications exists. In specific embodiments a time gaps should not exceed 30 minutes.

According to one aspect, a first composition is formulated to comprise actives which up-regulate an eigengene derived from a co-expression module formed from the intersection of a "younger appearance" module and one or more modules associated with biological pathways relating to cleansing, hydrating and detoxification pathways/processes. Non-limiting examples include autophagy, endopeptidase activity and proteolysis (see FIG. 2, Table 1).

In another aspect, a second composition is formulated to comprise one or more actives which up-regulate an eigengene derived from a co-expression module formed from the intersection of an age related module and one or more modules associated with biological pathways related to repair and rebuilding pathways/processes, for example DNA repair, cell adhesion, lipid and amino acid synthesis (see FIG. 2, Table 2).

It should be noted that for purposes of illustration of the fundamental principles upon which the invention is based, particular actives are disclosed and discussed; however it is contemplated that any active may be similarly evaluated, categorized, and utilized in a presently inventive regimen designed for enhanced anti-aging effects.

An exemplary first composition comprises skin actives selected from Pal-KT ((palmitoyl-lysine-threonine) and Glyco-Repair™ (a brand of carob seed extract) and combinations thereof. An exemplary second composition comprises skin actives selected from Pal-KTTKS (palmitoyl-lysine-threonine-threonine-lysine-serine), Olivem® 460 (a brand of olive oil extract), Lys'lastine® V (a brand of dill extract) and combinations thereof.

As demonstrated in (Prophetic) Example 4, application according to a first regimen comprising topical application of the first formulation prior to the second composition results in an enhanced anti-aging effect when compared to application according to a second regimen comprising application of the second composition prior to the first composition. The enhancement, however, is maximum if the time between applications is 1-10 minutes and diminishes to zero if there is a gap in time between applications of greater than about 30 minutes. Notably, younger looking skin is achieved by both regimens; however there is a statistically significant benefit to application according to the first regimen over the second regimen. This effect is independent of delivery vehicle.

Without being bound by theory, the present investigators hypothesize that the statistically significant difference may be due to interplay between the biological processes/pathways activated by each formulation. For example, as skin ages many changes occur within the cells/tissue, including the accumulation of proteins damaged from repeated stress from both internal insults and external insults such as exposure to UV radiation. In one example of positive interplay, the overall processes of rebuilding and renewing the skin's structural components may be maximized by first cleaning, hydrating and detoxifying damaged material from skin cells like keratinocytes and fibroblasts so that newly formed structural components can be integrated into renewed tissue. In another example of positive interplay, hydration of the skin by the first composition may also contribute to an enhanced effect of the second composition. A highly hydrated cellular environment favors optimal enzyme activity associated with the biological pathways implicated in cleaning and detoxification. In one very specific example, an active that triggers proteolytic processes is formulated into the first composition, while a neutralizer is formulated together with other peptide actives in the second composition so that the other peptide actives are not subjected to the enzymatic/degradative effects of proteolytic enzymes triggered by application of the first composition. According to very specific embodiments of the invention, the first composition comprises a dipeptide active and the second composition comprises an olive extract is formulated together with longer peptides, such as palmatoyl-pentapeptides, in order to preserve the rebuilding activity of the pentapeptide active. In a very specific embodiment the first composition comprises Pal-KT and the second composition comprises Olivem® 460 and Pal-KTTKS.

In another example of affirmative interplay between biological processes achieved by a specific embodiment of the regimen, a hydrated skin environment may be created from application of the first composition. According to aspects of this embodiment, an olive oil extract is included in the second composition to aid in delivery of other actives, especially larger peptides, to epidermal and dermal compartments where activation of repair and rebuilding processes/pathways, including DNA repair, cell adhesion, lipid and amino acid synthesis may occur. According to specific embodiments the first composition comprises a carob seed extract and/or a dipeptide to impart a hydrated status to the skin prior to application of the second composition, which comprises olive oil extract in combination with one or more actives selected from a pentapeptide, a dill extract, a vitamin B3 compound, and combinations thereof. In very specific embodiments a first composition comprises Pal-KT and Glyco-Repair™ brand carob extract, and a second composition comprises Olivem® 460 brand olive oil extract, Pal-KTTKS, niacinamide, and Lys'lastine® V brand dill extract.

Kits are also provided. According to one embodiment a cosmetic skin treatment kit comprising a first skin care composition and a second skin care composition separately contained. The first composition is formulated to comprise at least one active possessing an ability to transcriptionally up-regulate an eigengene derived from a genetic co-expression module for one or more biological themes associated with skin cleansing and/or skin detoxification to the target portion of skin, and the second composition is formulated to comprise at least one active possessing an ability to transcriptionally up-regulate an eigengene derived from a co-expression module for one or more biological themes associated with skin repair and/or rebuilding, instructions to apply the first composition to a target area of skin prior to applying the second composition to the target area of skin. The kit may optionally include at least one applicator to effectuate topical application of the first and/or the second skin care composition to the target area of skin. Kits according to specific embodiments of the invention include those wherein the biological theme associated with skin cleansing and/or skin detoxification are selected from a biological theme set forth in FIG. 2, Table 3, and wherein the one or more biological themes associated with skin repair and/or rebuilding are selected from a biological theme set forth in FIG. 2, Table 2.

A first composition of a specific kit embodiment is formulated to comprise actives selected, for example, for possessing an ability to transcriptionally up-regulate an eigengene derived from a genetic co-expression module for one or more biological themes associated with skin cleansing and/or skin detoxification. In very specific embodiments the actives comprise one or more of a palmitoyl peptide derivative and a carob seed derivative, and in more specific embodiments the palmitoyl peptide derivative comprises Pal-KT and the carob seed derivative comprises Glyco-Repair™. A second composition of a specific kit embodiment is formulated to comprise at least one active possessing an ability to transcriptionally up-regulate an eigengene derived from a co-expression module for one or more biological themes associated with skin repair and/or rebuilding. According to very specific embodiments the actives are selected from one or more of a palmitoyl peptide derivative, a vitamin B3 compound, a dill extract derivative and an olive oil derivative, and in more specific embodiments the palmitoyl peptide derivative comprises Pal-KTTKS, the vitamin B3 compound comprises niacinamide, the dill extract derivative comprises Lys'lastine® V and the olive oil derivative comprises Olivem® 460.

The kit may include at least one applicator, and in some embodiments the kit comprises different applicators for each formulation. The applicator may be part or integral to the formulation container, or may be detachably removable or disposable or re-usable, or may be an independent applicator. Applicators for topical application of skin care compositions are well known in the art.

Methods for identifying an agent effective for transcriptionally up-regulating an eigengene associated with a desirable cosmetic phenotype of human skin are also disclosed. The method comprises: deriving an eigengene for a co-expression module determined from a set of genes transcriptionally up-regulated in human skin exhibiting the desirable cosmetic phenotypic and a set of genes associated with one or more biological themes; treating skin with a putative agent; conducting a transcriptional assessment of the eigengene in the treated skin; and identifying the putative agent as an effective agent if the eigengene is up-regulated in the treated skin. It is contemplated that the foundational principles of this invention are applicable to provide regimens with enhanced benefit for a number of cosmetic concerns in addition to anti-aging effects.

Exemplary actives formulated in compositions according to particular regimen embodiments are discussed in more detail below; however it should be understood that other actives identified as effective in accordance with aspects of the invention may be included in the compositions in addition to or in replace of the exemplary actives, which are set forth merely to illustrate the foundational principles of the invention.

Olive Oil Extract/Derivatives

Olive oil extract/derivatives such as OLIVEM® brand olive oil derivatives are believed to provide, inter alia, anti-oxidant activity, and other neutralizing activity, which may lead to protection against environmental assaults (see, e.g., Skin Biomarkers Confirm the Anti-Oxidant Activity of Olive Derivatives and Yeast Ferment Filtrate, Finlay et al., P&G 67th Annual Meeting of American Academy of Dermatology (2009)). Specific olive oil extracts/derivatives include the sodium PEG-7 olive oil carboxylates available from B&T SRL as Olivem® 400, Olivem® 450 or Olivem® 460.

OLIVEM® 460 is an extremely mild olive-based surfactant designed with 60% (Free-Preservation System) active concentration. It is an anionic surfactant derived from olive oil with foaming, cleansing and solubilising properties. It exhibits nonionic behavior in solution. Its foam is creamy, small bubbled and cleanses mildly. Olive oil extract may be included in compositions in amounts of between 0.1 ppm and 5 ppm, 0.25 ppm and 3 ppm, and 0.5 ppm and 2.5 ppm or as 0.0005-0.01% by weight. In very specific embodiments, compositions comprise 0.63 ppm, 2.5 ppm, or 0.001% Olivem® brand olive oil extract.

Vitamin B3 Compounds

Vitamin B3 compounds are known skin care actives and are believed to provide a number of cosmetic skin care benefits (see, e.g., Bissett el al. "Niacinamide: A B Vitamin that Improves Aging Facial Skin Appearance" and Draelos "Clinical Situations Conducive to Proactive Skin Health and Anti-Aging Improvement"). Vitamin B3 compounds are known as possessing an antioxidant and a skin-lightening effect. Composition aspects of the invention may include one or more vitamin B3 compounds, and salts and derivatives thereof. Non-limiting examples of suitable vitamin B3 compounds include nicotinic acid esters, including non-vasodilating esters of nicotinic acid, nicotinyl amino acids, nicotinyl alcohol esters of carboxylic acids, nicotinic acid N-oxide, niacinamide, their salts and derivatives, and mixtures thereof. In specific embodiments, the vitamin B3 compound is niacinamide.

The compositions may comprise from about 0.01% to about 50%, alternatively from about 0.1% to about 10%, alternatively from about 0.5% to about 10%, alternatively from about 1% to about 5%, and alternatively from about 2% to about 5%, of the vitamin B3 compound by weight of the composition. According to specific embodiments compositions are formulated to comprise 250 μM niacinamide.

Carob Fruit Extract

The carob fruit extract (INCI name: Ceratonia siliqua fruit extract; CAS Number: 84961-45-5) of the present invention is made from the oblong, non-fleshy, bean-like pod that grows on the carob tree, which belongs to the legume family Fabaceae. Carob is rich in oligogalactomannans, which are believed to be important biological actives. The carob fruit pod contains large seeds commonly referred to as "carob nuts". Carob fruit extract suitable for use herein can be derived from the fruit pod, the seeds, or combinations thereof, using processes known in the art. The carob fruit extract may include other suitable materials such as, for example, water, thickeners, humectants, solvents, solubilizers, etc. A suitable carob fruit extract for use herein is commercially produced by Silab S.A. (France), under the trade name Glyco-Repair™. This particular extract product contains approximately 94% water, 5% carob fruit extract, and 1% other materials.

The carob fruit extract may be included in the composition herein at an amount of from 0.0001% to 15%, from 0.0002% to 10%, from 0.001% to 15%, from 0.025% to 10%, from 0.05% to 10%, from 0.05% to 5%, or even from 0.1% to 5%, by weight of the total composition. In very specific embodiments Glyco-Repair™ brand carob fruit extract is included at 1% by weight of the composition.

Dill Extract

Some composition aspects of the present invention may comprise one or more types of dill extract, known for providing cosmetic benefits to skin including improved skin elasticity and increased skin firmness. As used herein, "dill extract" refers to dill, dill seed, dilly, peucedanum graveolens, anethum graveolens, anethum sowa, and related synthetic and derivative materials.

Dill extract restores elastin functionality and activates LOXL (the major component in skin elasticity during aging) synthesis. Restoration of LOXL levels in aged skin can restore the skin's elasticity and firmness and prevent sagging. An aqueous extract of dill has been found to be an active, dose-responsive and reproducible material, producing a 2-fold increase in LOXL gene expression (RT-PCR) and 1.5-fold increase in elastin gene expression. In a proprietary 3-D skin model (Mimeskin™ skin model of BASF BC), 0.0750% dill extract produced a significant ($p<0.001$) increase in LOXL mRNA (64%) and LOXL protein (12%) at four weeks, producing microfilaments containing elastin as detected by transmission electron microscopy. Dill extract (0.0750%) produced a significant ($p<0.01$) 29% increase in elasticity versus a control after four weeks.

Composition aspects of the invention may comprise about 0.001% to about 7.0% dill extract, more specifically from about 0.01-5.0%, and most specifically from about 0.05-2.5% by weight of the composition. In a very specific embodiment, the dill extract is present as peucedanum graveolens in Lys'lastine® V, commercially available from BASF and is included as 1% by weight of a composition.

Peptides and Peptide Derivatives

The composition aspects of the present invention may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. Peptides may be di-, tri-, tetra-, penta-, and hexa-peptides, their salts, isomers, derivatives, and mixtures thereof. Examples of useful peptide derivatives include, but are not limited to, peptides derived from soy proteins (Ridulisse C™, from Silab, France), carnosine (beta-alanine-histidine), palmitoyl-lysine-threonine (pal-KT) and palmitoyl-lysine-threonine-threonine-lysine-serine (pal-KTTKS, available in a composition known as MATRIXYL® which contains 100 ppm of pal-KTTKS), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EEMQRR; Argireline®), and Cu-histidine-glycine-glycine (Cu-HGG, also known as IAMIN®).

Certain peptides such as PAL-KT are widely recognized as skin care actives that can provide skin anti-aging benefits, such as an improvement in the appearance of fine lines and wrinkles (see, e.g., In Vitro Biomarker Responses to a New Anti-Aging Peptide, PAL-KT, Osborne et al, American Academy of Dermatology 67th Annual Meeting Media Resources, 2009). Compositions may comprise from about $1 \times 10^{-6}$% to about 20%, alternatively from about 0.01% to about 10%, alternatively from about 0.1% to about 5% of a peptide, and alternatively from about 1 to about 2%. In a specific embodiment, the composition may comprise from about 0.1% to about 2% of a peptide. In specific embodiments utilizing the pentapeptide-containing composition, Matrixyl®, the resulting composition contains from about 0.01% to about 50%, more preferably from about 0.05% to about 20%, and even more preferably from about 0.1% to about 10%, by weight of the resulting composition, of Matrixyl®.

Compositions according to aspects of the invention may comprise a wide variety of additional and optional ingredients without departing from the spirit of the invention. In particular, optional ingredients suitable for use herein include any ingredient known for safe use in cosmetic compositions (e.g., emollients, humectants, vitamins; peptides; and sugar amines, sunscreen actives (or sunscreen agents), ultraviolet light absorbers, colorants, surfactants, film-forming compositions, and rheology modifiers). Some non-limiting examples of suitable optional ingredients for use in the present compositions are disclosed in U.S. Publication No. US2008/0206373, filed by Millikin, et al., on Feb. 28, 2008, U.S. Pat. Nos. 5,997,890, 6,492,326, and 6,696,049, all directed to cosmetic skin care compositions, the entire disclosures of which are incorporated herein by this reference. Illustrative compositions in accordance with very specific embodiments of the invention are set forth in Example 4.

Although specific embodiment range points for the exemplary actives include lower range values, it is understood that a composition according to some embodiments of the invention may not include any particular active and that the ranges apply where an active is included according to overall formulation design.

EXAMPLES

The following Examples collectively illustrate aspects of an inventive regimen in accordance with specific embodiments. In particular, the examples demonstrate that an enhanced anti-aging effect on skin is achieved by application of multiple compositions, each composition comprising a different set of actives, and applied in a specific regimen sequence versus a reverse sequence versus application of a single composition comprising all actives. Each independent composition is formulated to comprise actives selected according to a biological processes implicated by the active in an assessment using eigengene analysis based on eigengenes derived from co-expression modules for "young appearance" related genes and biological process/pathway genes. The implicated themes complement one another when activated in specific sequence and may exhibit some counter-active effects in reverse sequence.

Example 1

The following Example illustrates differences in age dependency of the facial epidermis and epidermis transcriptome among women perceived to look "younger," "average" and "older" in appearance than their chronological age, and generation of the "younger appearance" expression module and eigengene representing the model.

Figure 3:
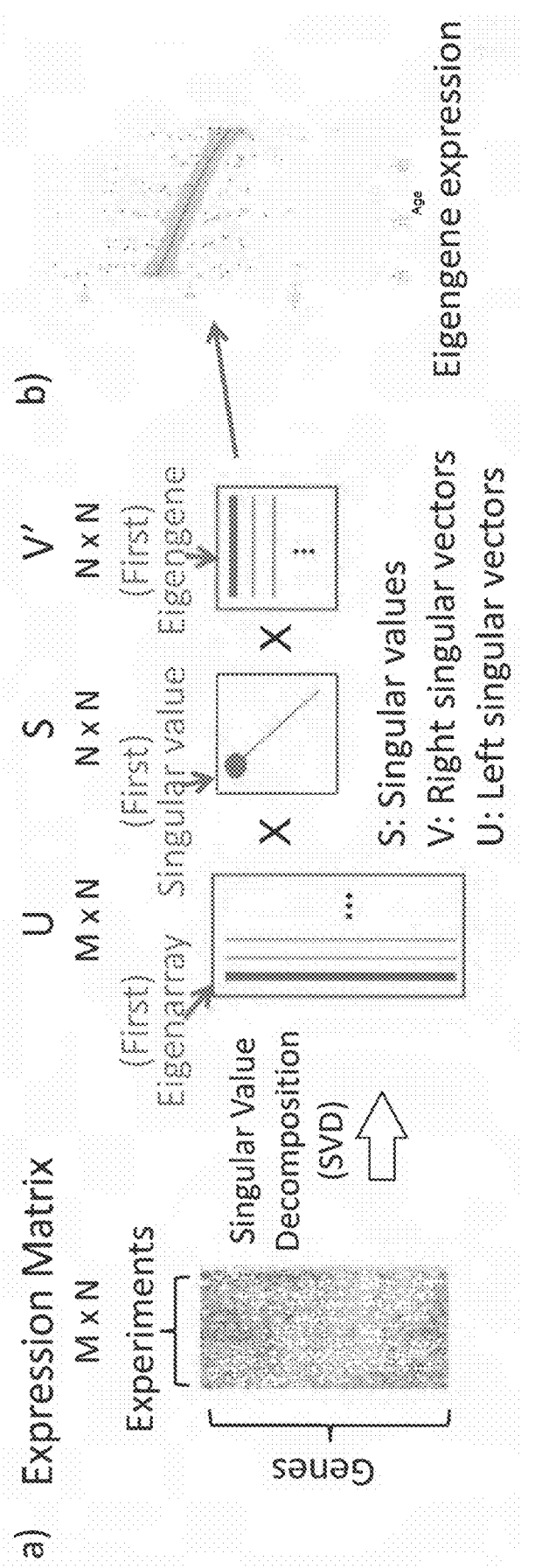
FIG. 3. Schematic depicting derivation of an Eigengene representation.

Facial skin biopsies were obtained from female volunteers ranging in age from 20 to 70. RNA was extracted from epidermis and dermis tissues using laser capture microdissection. Transcriptomic profiles were obtained using Affymetrix HG-U219 probe arrays. "Perceived appearance age," also referred to herein as "apparent age" was extrapolated on consensus in relative scores of facial digital images from naïve graders and the subject population was grouped into three categories of agers, with the bottom 30% of the subjects designated as unsuccessful, the middle 40% designated as average, and top 30% designated as successful agers. As depicted in FIGS. 1A and 1B, nearly 2000 genes were found to have a significant association (p-value<0.05) with perceived appearance by ANOVA and ANCOVA regression models. FIG. 1A sets forth the "younger-appearance" module associated with the epidermis while FIG. 1B sets forth the younger-appearance module associated with the dermis. Derivation of an eigengene in accordance with embodiments of the invention is depicted schematically in FIG. 3. Twenty-six over-represented biological themes were identified based on gene set enrichment analysis (FIG. 2) from the epidermis sample.

Example 2

In order to evaluate treatment effects of cosmetic actives on appearance associated genes in vitro, transcriptome profiles were determined in cultured human keratinocytes treated with the particular cosmetic actives. Co-expression modules were determined for the "younger-appearance" gene set module and each of several biological process/theme modules. Singular value decomposition was applied to the transcriptome profile for co-expression module in order to obtain its eigengene, representing the major expression variance across all subjects. Treatment effects of exemplary cosmetic actives including niacinamide, pal-KT, pal-KTTKS, Lys'lastine® V brand dill extract, Olivem® 460 brand olive oil extract, Glyco-Repair™ brand carob fruit extract and H26 were evaluated by determining the impact of treatment on the eigengene. The biological processes studied included Cell Adhesion, Skin Barrier, Energy-related, and Age-related. Each of these processes has a gene set previously identified as associated with themes or pathways within the process category. One goal of these studies is to determine which actives should be included in which regimen step in accordance with embodiments of the invention. Efficacy for a particular biological process or theme and identification of that theme as predominantly part of a "cleanse, hydrate and detox" function or predominantly part of a "repair and rebuild" function is a factor in determining whether an active should be formulated into an anti-aging regimen step 1 or step 2.

Figure 4:
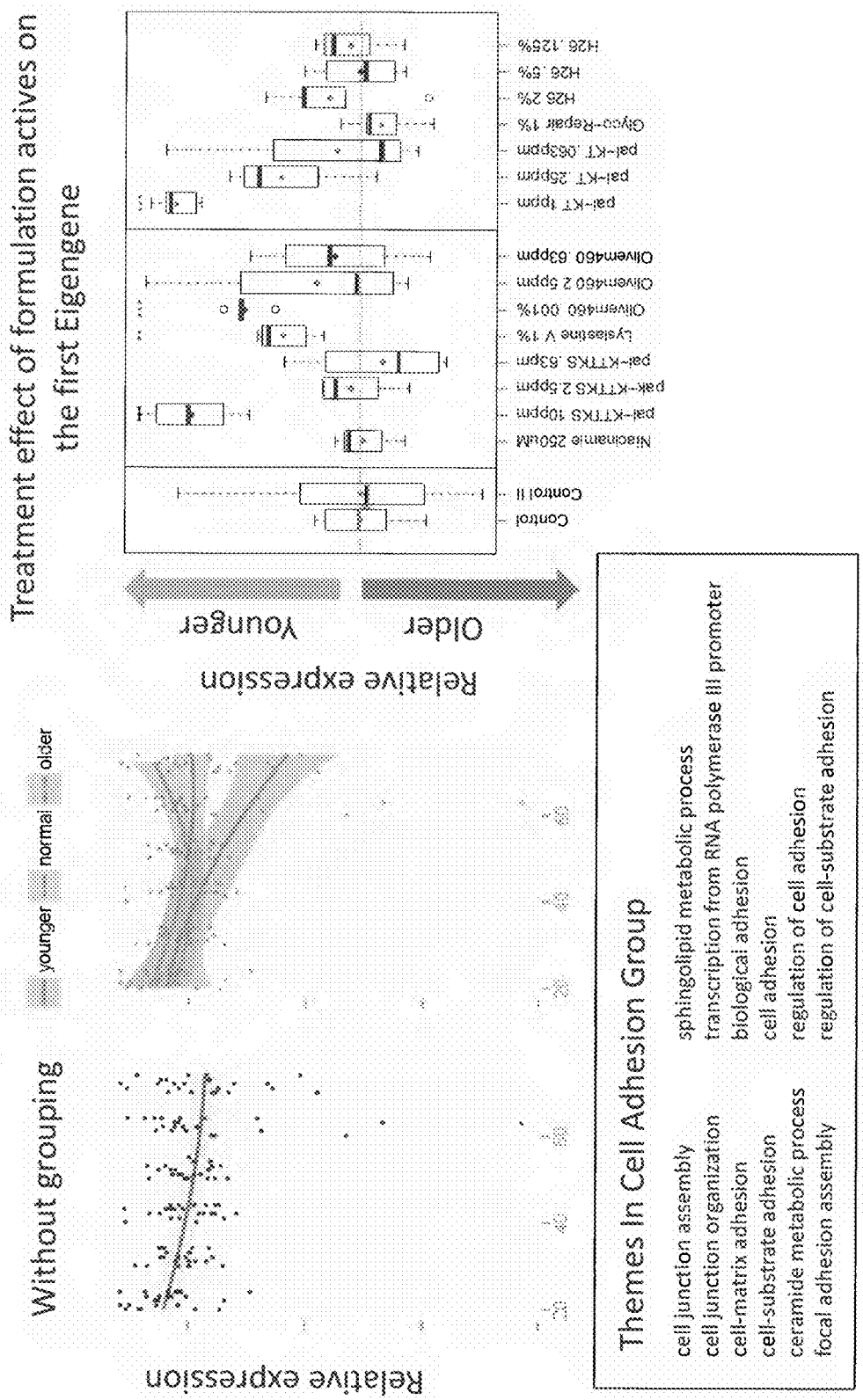
FIG. 4. Graph of Eigengene of co-expression module for "younger-appearance" and "Cell Adhesion" and chart showing effects of exemplary actives on Eigengene.
Figure 5A:
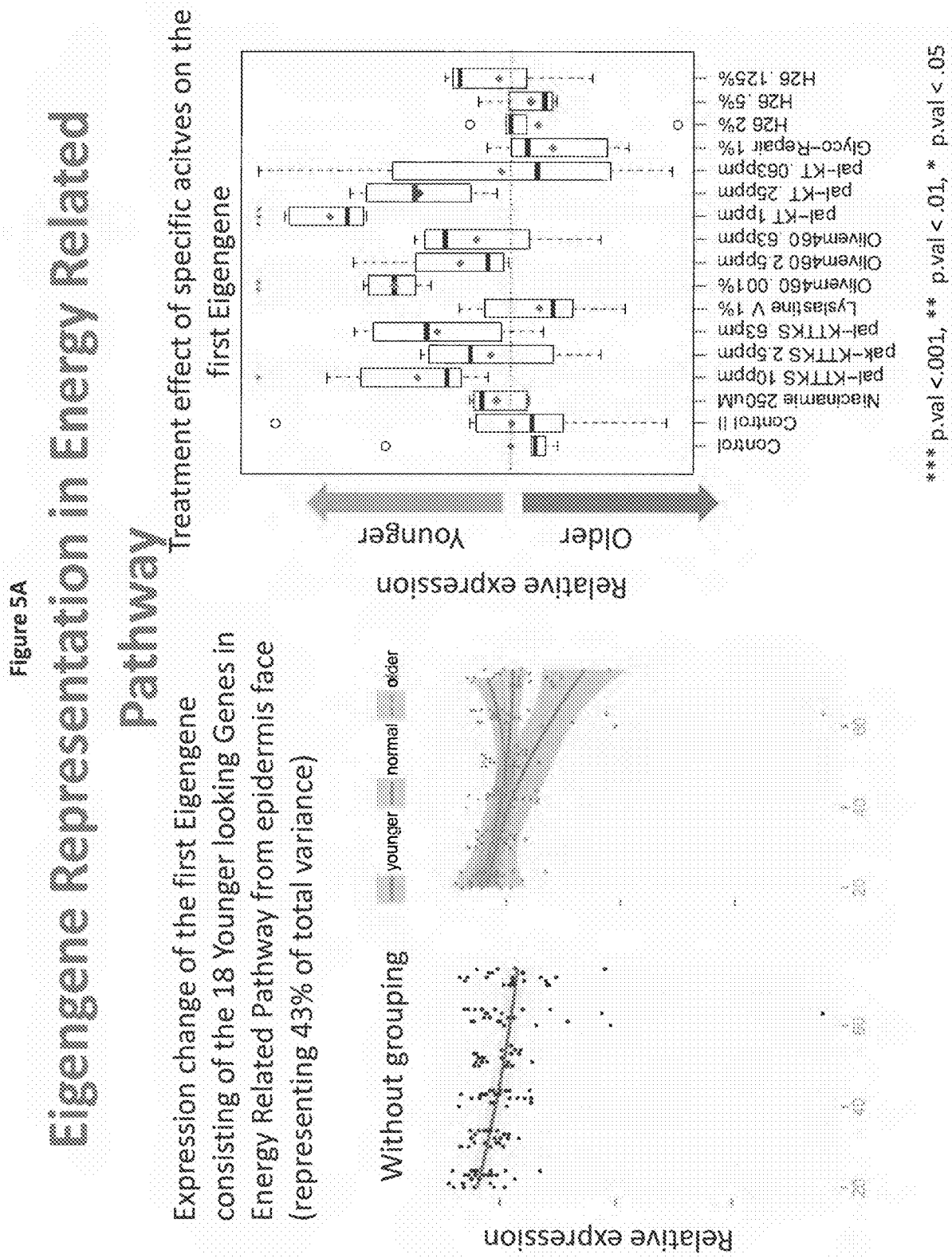
Figure 6B:
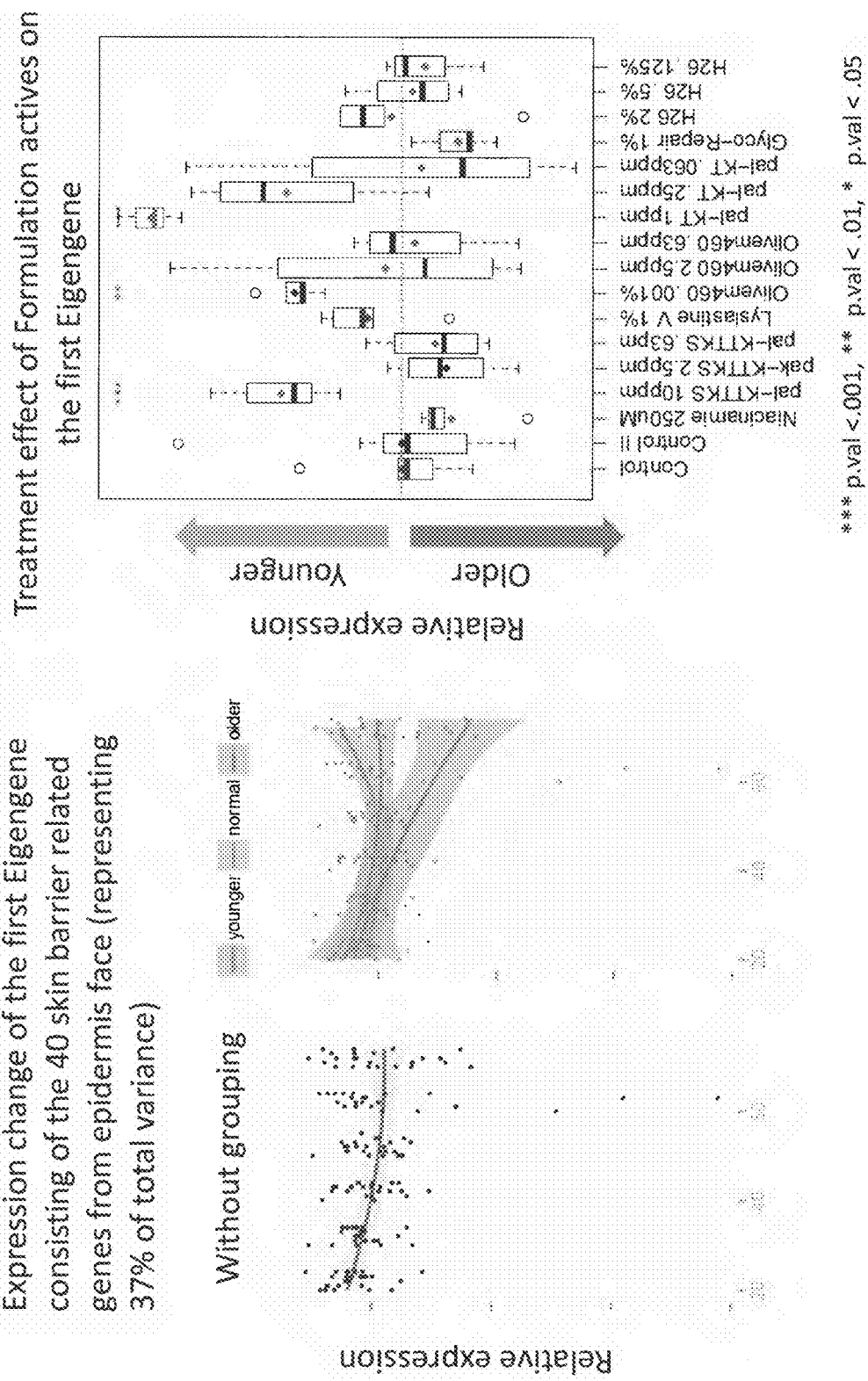
Figure 7B:
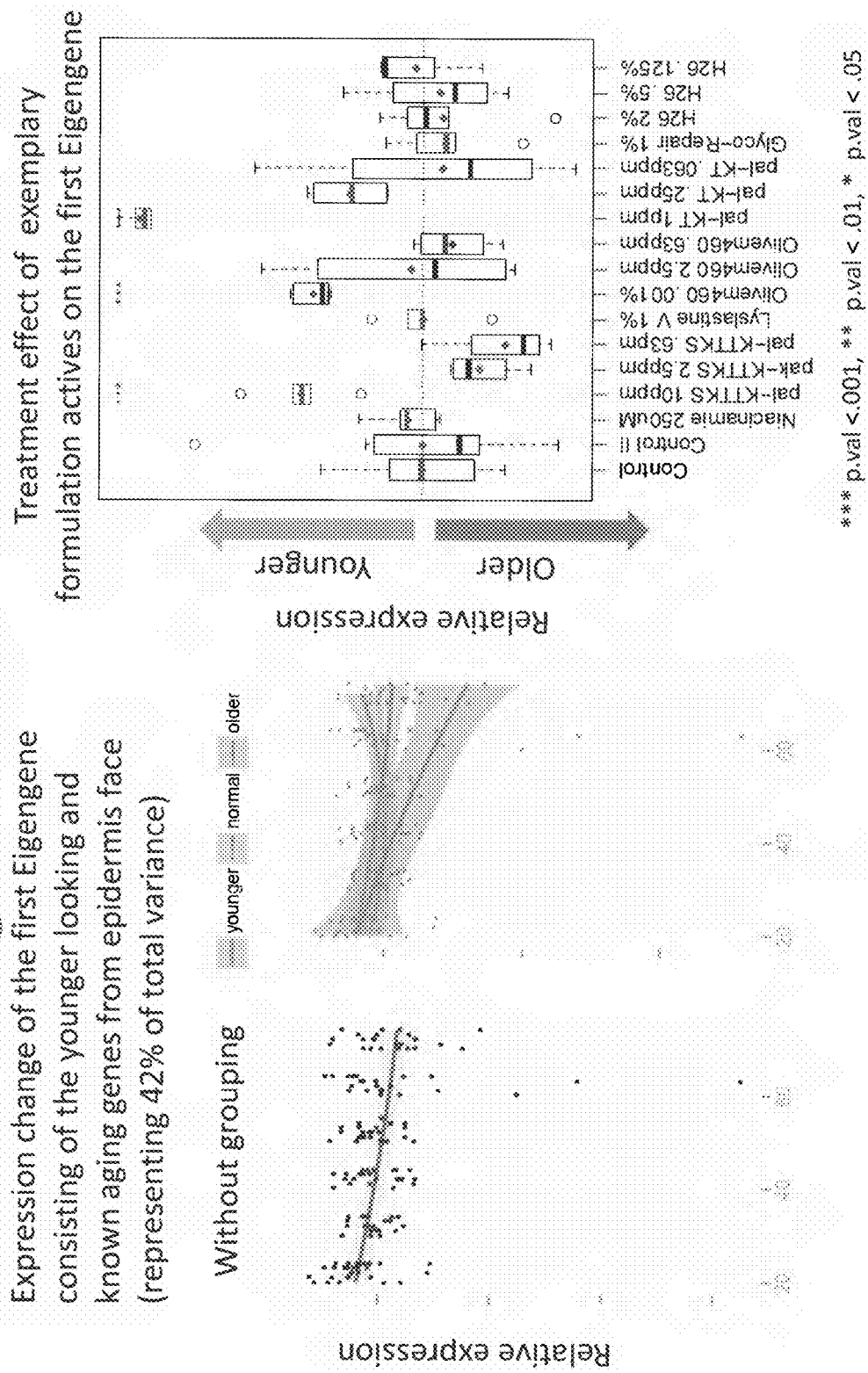

The eigengene representation of "younger-appearance" genes in Cell Adhesion processes is depicted in FIG. 4. The effect of seven exemplary cosmetic actives in various concentrations, as well as control vehicle, on the eigengene is also illustrated. A "successful-aging effect" is defined by the treatment effect on the eigengene. For example in FIG. 4, an eigengene for the "Cell Adhesion and Junction" theme shows that expression level goes down with aging in the older-appearance individuals, but much less in normal, and almost no change is observed in younger looking individuals. The box plot to the right in FIG. 4 shows that both pal-KT and pal-KTTKS significantly up-regulate the eigengene, which indicates that these actives support successful aging via effect on the "Cell Adhesion and Junction" theme Similarly, the eigengene representation of "younger-appearance" genes in Energy-related processes and effects on the eigengene of exemplary actives is depicted in FIGS. 5A and 5B. The eigengene representation of "younger-appearance" genes in "Skin barrier" function and effects on the eigengene of exemplary actives is depicted in FIGS. 6A and 6B. The eigengene representation of "younger-appearance" genes in "age-associated" processes and effects on the eigengene of exemplary actives is depicted in FIGS. 7A and 7B.

Notable observations from these studies include that Pal-KTTS and Olivem® 460 were observed to significantly increase eigengene expression associated with cell junction assembly and cell adhesion processes, suggesting that pal-KTTS and Olivem® 460 treatment promote successful aging of facial appearance via these biological processes.

Effects relating to successful aging were also identified for Pal-KT in skin barrier formation, Lys'lastine® V in defense responses, and Glyco-Repair™ in protein transport processes. The results suggest that formulating compositions with certain combinations of actives may provide benefits through complimentary processes.

Example 3

Figure 9:
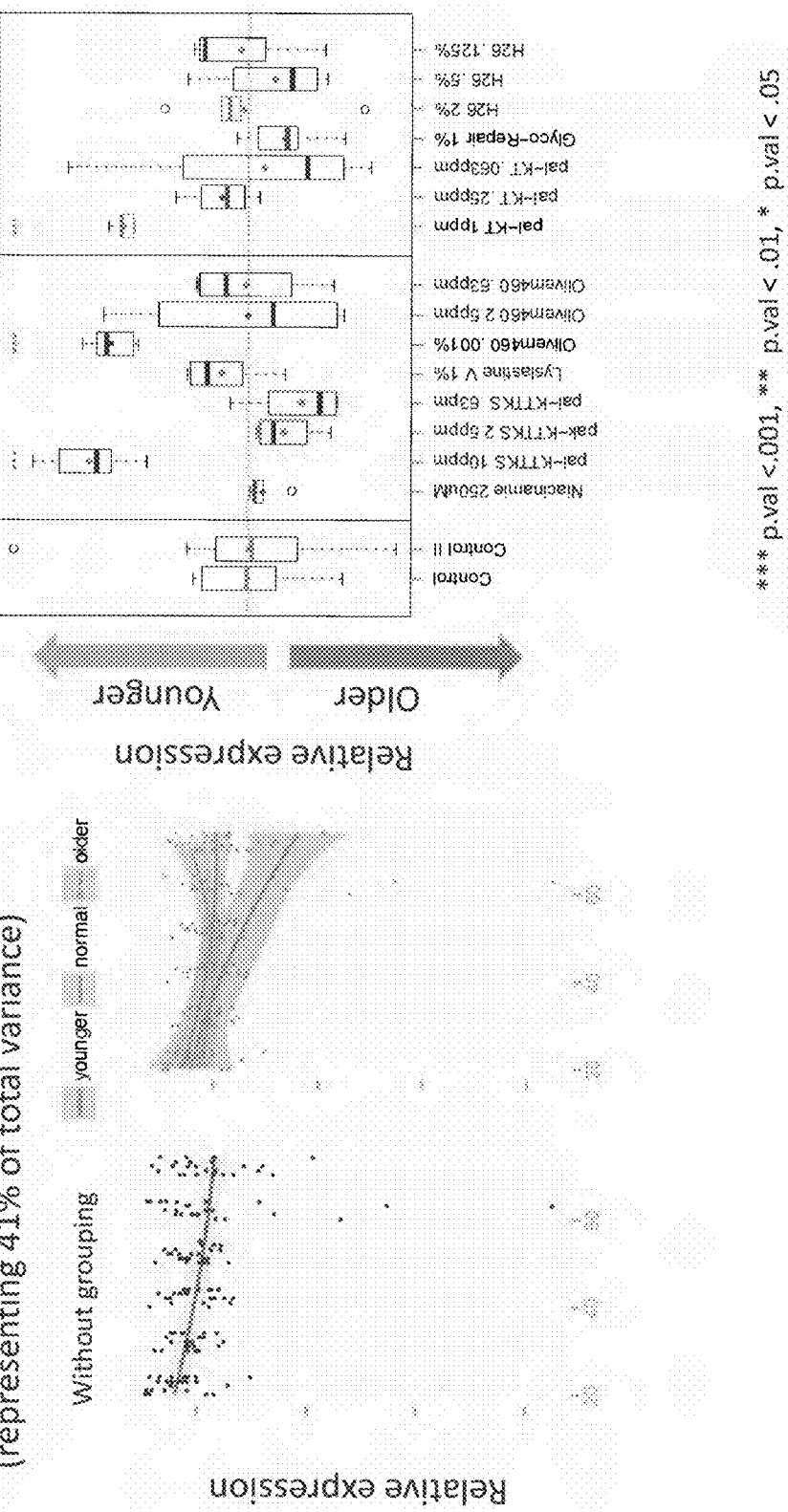
FIG. 9. Graph and chart showing Eigengene representation of "Repair and Rebuild" related genes.
Figure 10:
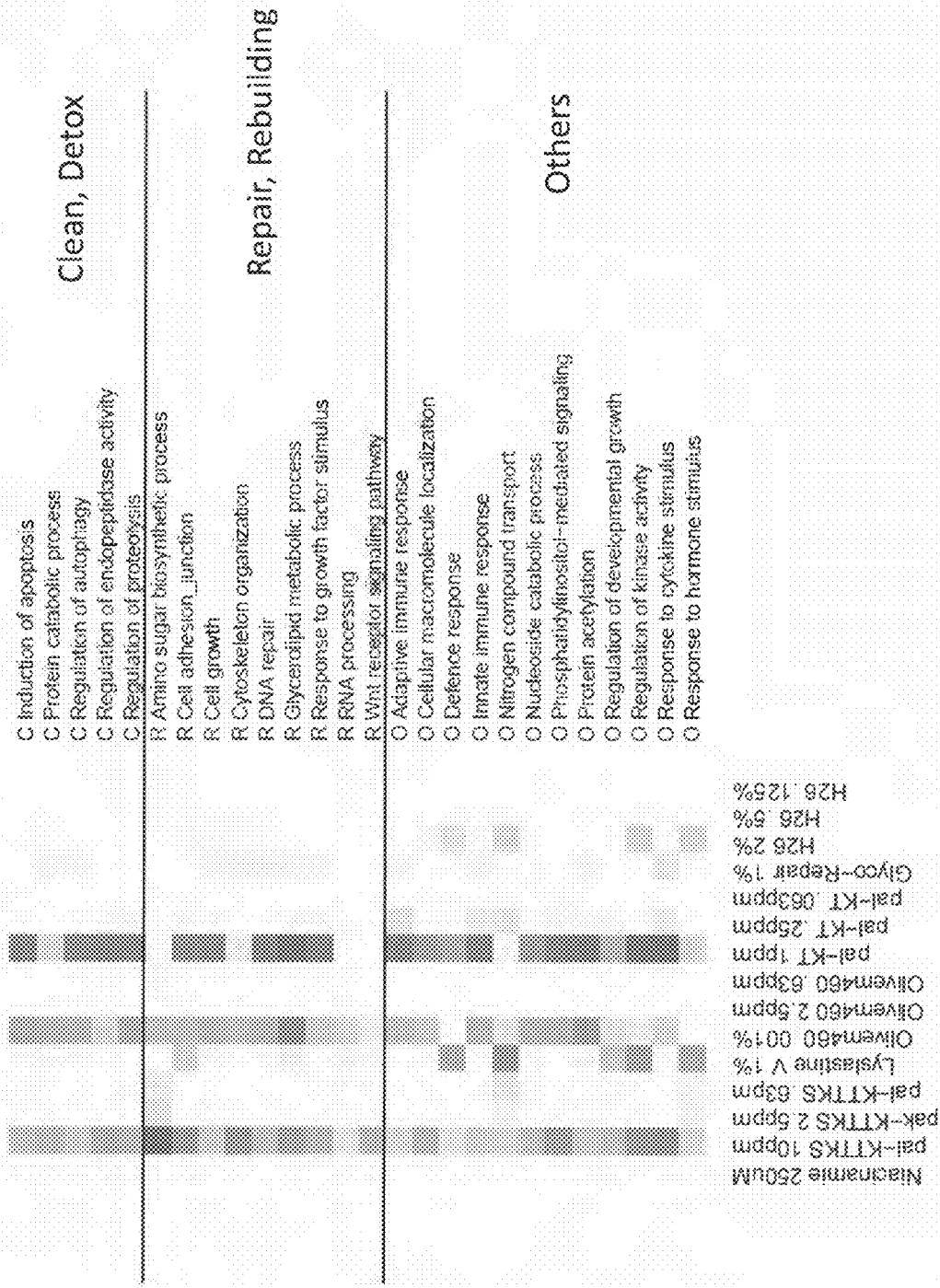
FIG. 10. Heat Map of an anti-aging effect of exemplary actives according to biological theme.

The following Example illustrates derivation of an eigengene representing genes associated with biological processes/themes relating to cleaning, hydration and detoxification processes (FIG. 8) and derivation of an eigengene representing genes associated with biological processes/themes relating to skin repair and rebuilding (FIG. 9), and evaluation of the treatment effect of different skin care actives on the eigengenes (FIG. 10). Generated data was re-grouped to evaluate which actives should be included in specific steps of an anti-aging regimen. Two formulations were selected for a comparison study based on eigengene analysis of co-expression modules derived from appearance genes and process genes.

The exemplary actives were divided into two proposed compositions based on whether the biological processes implicated by each fell within one of two general groups. In the general analysis the 26 themes are grouped into "Clean and Detox", "Repair and Rebuild", and "Others". The "Clear and Detox" group includes themes having a scavenging and recycling role, such as protein catabolic processes and autophagy, while the "Repair and Rebuild" group includes themes of skin development and repairing processes such as cell adhesion, junction, and DNA repair. Genes and corresponding probe sets involved in these themes and groups are set forth in Table 4.

Figure 8:
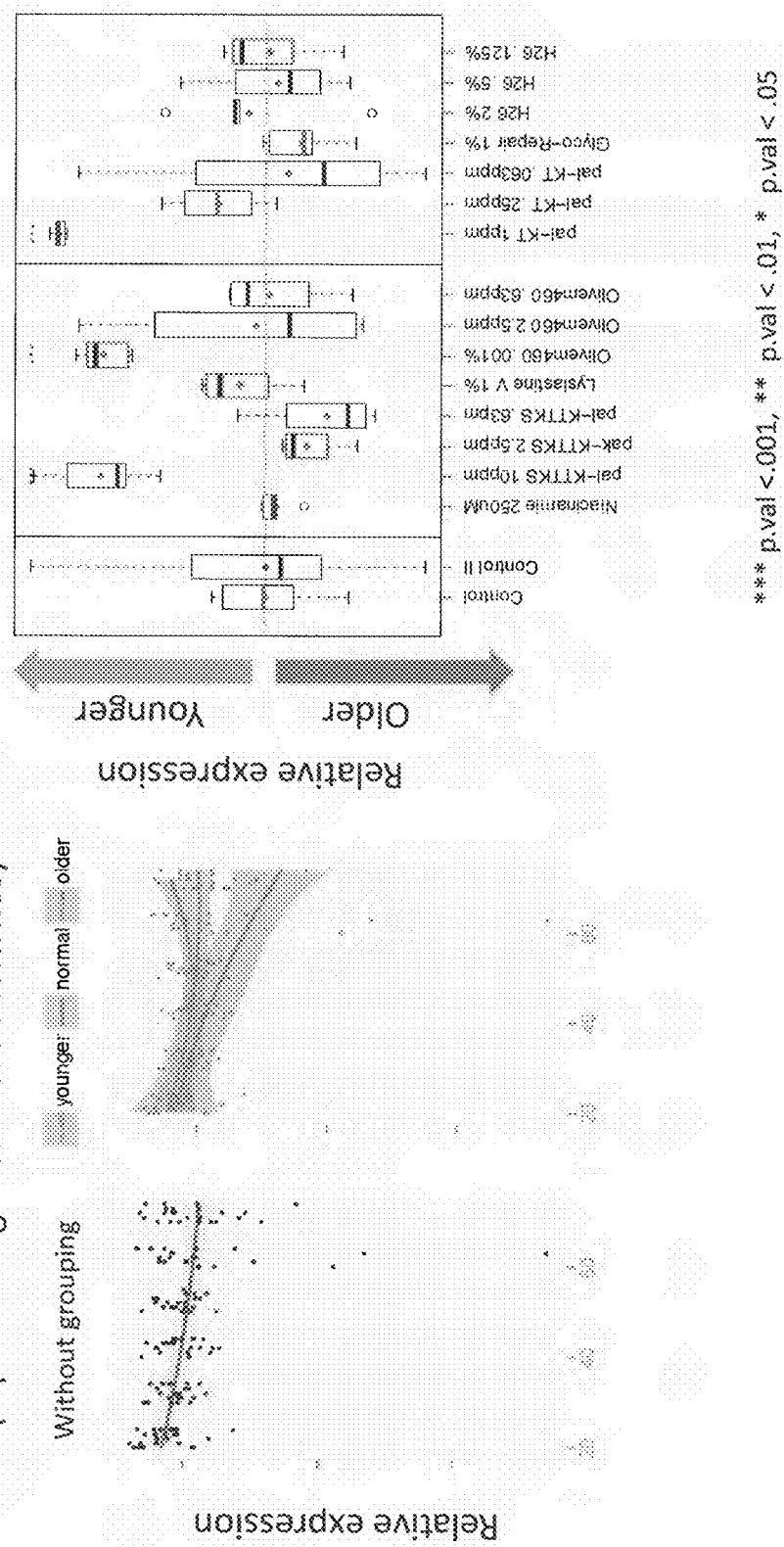
FIG. 8. Graph and chart showing Eigengene representation of "Clean and Detoxification" related genes.

FIG. 8 shows that an eigengene derived from the co-expression module for "Clear and Detox" and each of the three Appearance modules shows a different age dependency among appearance groups with the magnitude decreasing at a greater rate among the older appearance individuals. Pal-KT significantly up-regulates the eigengene, which indicates that pal-KT treatment supports successful aging via the "Clear and Detox" module genes. Pal-KTTKS and Olivem® 460 also up-regulate the eigengene, but to a lesser extent than pal-KT.

An eigengene derived from the co-expression module consisting of 301 "Repair and Rebuild" associated genes (FIG. 9) also shows the similar pattern of "Clear and Detox" (FIG. 8). In this group, pal-KTTKS and Olivem® 460 significantly up-regulate the eigengene, indicating that pal-KTTKS and Olivem® 460 treatment support successful aging via the "Rebuild and Repair" related genes. pal-KT also up-regulated the eigengene, but to a lesser extent than Pal-KTTS and Olivem® 460. FIG. 5 shows that Pal-KT and Olivem® 460 demonstrate a strong anti-aging benefit on the overall appearance associated genes.

Further, individual actives were inspected for mechanism compatibility. FIG. 10 sets forth a Heat Map demonstrating successful-aging effects for both proposed compositions independent of one another. The composition actives are plotted against the impacted themes, where intensity indicates the strength of effect, and red and blue points indicate positive and negative effect, respectively.

Example 4

The following Example provides illustrative compositions in accordance with aspects of the invention. A regimen step is referred to "step 1" if it is applied to a target area of skin as part of an at least two-step regimen, and a regimen is referred to as "step 2" if it is applied to the target area of skin after a step 1 composition, although it is understood that additional activities, non-limiting examples including rinsing and/or drying, may be undertaken before, between and/or after a regimen steps 1 and 2.

Formulation Examples

SC99 (Oil-in-Water Emulsion) Base Product Regimen Step 1

| Ingredient | Example 1 (wt. %) | Example 2 (wt. %) | Example 3 (wt. %) | Example 4 (wt. %) |
| --- | --- | --- | --- | --- |
| Water | 88.88 | 86.48 | 81.98 | 75.93 |
| Glycerin | 3 | 5 | 7 | 10 |
| Thickener (Sepigel 305) | 1 | 1 | 2 | 2 |
| Isopropyl isostearate | 1 | 1 | 1 | 1 |
| Isohexadecane | 3 | 3 | 3 | 3 |
| Cetyl alcohol | 0.3 | 0.3 | 0.3 | 0.3 |
| Stearyl alcohol | 0.5 | 0.5 | 0.5 | 0.5 |
| Dimethicone (DC Q2-1503) | 2 | 2 | 2 | 2 |
| Ethylparaben | 0.15 | 0.15 | 0.15 | 0.15 |
| Propylparaben | 0.07 | 0.07 | 0.07 | 0.07 |
| Pal-KT | 0.0002 | 0.0005 | 0.005 | 0.05 |
| Glyco-repair ™ | 0.1 | 0.5 | 2 | 5 |

SC99 (Oil-in-Water Emulsion) Base Product Regimen Step 2

| Ingredient | Example 5 (wt. %) | Example 6 (wt. %) | Example 7 (wt. %) | Example 8 (wt. %) |
| --- | --- | --- | --- | --- |
| Water | 87.93 | 86.78 | 82.97 | 78.44 |
| Glycerin | 3 | 5 | 7 | 10 |
| Thickener (e.g. Sepigel 305) | 2 | 1 | 2 | 2 |
| Isopropyl isostearate | 1 | 1 | 1 | 1 |
| Isohexadecane | 3 | 3 | 3 | 3 |
| Cetyl alcohol | 0.3 | 0.3 | 0.3 | 0.3 |
| Stearyl alcohol | 0.5 | 0.5 | 0.5 | 0.5 |
| Dimethicone (DC Q2-1503) | 2 | 2 | 2 | 2 |
| Ethylparaben | 0.15 | 0.15 | 0.15 | 0.15 |
| Propylparaben | 0.07 | 0.07 | 0.07 | 0.07 |
| Olivem ® | 0.0005 | 0.001 | 0.005 | 0.01 |
| Pal-KTTKS | 0.0001 | 0.0003 | 0.003 | 0.03 |
| Lys lastine V ™ | 0.05 | 0.2 | 1 | 2.5 |
| Niacinamide | 2 | 3 | 4 | 5 |

SC800 (Silicone-in-Water) Base Product Regimen Step 1

| Ingredient | Example 9 (wt. %) | Example 10 (wt. %) | Example 11 (wt. %) | Example 12 (wt. %) |
| --- | --- | --- | --- | --- |
| Water | 79.55 | 78.15 | 73.65 | 67.6 |
| Glycerin | 3 | 5 | 7 | 10 |
| Thickener (Sepigel 305) | 2 | 1 | 2 | 2 |
| Dimethicone | 15 | 15 | 15 | 15 |
| Preservative | 0.3 | 0.3 | 0.3 | 0.3 |
| Disodium EDTA | 0.05 | 0.05 | 0.05 | 0.05 |
| Pal-KT | 0.0002 | 0.0005 | 0.005 | 0.05 |
| Glyco-repair ™ | 0.1 | 0.5 | 2 | 5 |

SC800 (Silicone-in-Water) Base Product Regimen Step 2

| Ingredient | Example 13 (wt. %) | Example 14 (wt. %) | Example 15 (wt. %) | Example 16 (wt. %) |
|---|---|---|---|---|
| Water | 77.6 | 75.45 | 70.64 | 65.11 |
| Glycerin | 3 | 5 | 7 | 10 |
| Thickener (Sepigel 305) | 2 | 1 | 2 | 2 |
| Dimethicone (DC-9041) | 15 | 15 | 15 | 15 |
| Preservative (Glydant Plus) | 0.3 | 0.3 | 0.3 | 0.3 |
| Disodium EDTA | 0.05 | 0.05 | 0.05 | 0.05 |
| Olivem ® | 0.0005 | 0.001 | 0.005 | 0.01 |
| Pal-KTTKS | 0.0001 | 0.0003 | 0.003 | 0.03 |
| Lys lastine V ™ | 0.05 | 0.2 | 1 | 2.5 |
| Niacinamide | 2 | 3 | 4 | 5 |

Example 5

The following PROPHETIC Example illustrates a regimen-based enhanced anti-aging benefit achieved by application of a composition formulated to target "Clear and Detox" processes prior to application of a composition formulated to target "Repair and Rebuild" processes by comparing effects achieved by different order regimens. Three compositions are formulated. Composition A comprises effective amounts of Pal-KT and Glyco-Repair™ brand carob fruit extract. Composition B comprises effective amounts of Olivem® 460 brand olive oil extract, Pal-KTTKS, Lys'lastine® V brand dill extract and niacinamide. Composition C comprises all actives in Compositions A and B. A control composition comprising delivery vehicle alone is also formulated. 3 Regimens with equal number of experimental and control subjects are evaluated. All dosing is once per day as part of morning routine over a treatment time frame of 7 weeks.

Regimen 1: apply A, rinse with water, immediately apply B;
Regimen 2: apply B, rinse with water, immediately apply A;
Regimen 3: apply C, rinse with water, immediately apply C.

120 women between the ages of 45 and 65 are recruited and cleared for potentially interfering conditions. A circumscribed area of target skin surround the eye is graded for age characteristic density by a digital program to provide a base for each subject. 20 experimental and 20 control subjects are assigned to follow each regimen. The test is run under a double-blind protocol. At the end of 7 weeks subjects are re-evaluated for age characteristic density of the target skin.

Results: For all regimens, the experimental group shows statistically significant improvement over the control group. The experimental group of Regimen 1 shows enhanced anti-aging benefit over the experimental group of Regimen 3, which shows greater anti-aging benefit over the experimental group of Regimen 2. These results demonstrate a surprising and unexpected enhanced anti-aging benefit as a function of order of application of scientifically-formulated compositions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A method for identifying an agent effective for transcriptionally up-regulating an eigengene associated with a desirable cosmetic phenotype of human skin, the method comprising:
    deriving an eigengene for a co-expression module determined from a set of genes transcriptionally up-regulated in human skin exhibiting the desirable cosmetic phenotype and a set of genes associated with a clean and detox biological theme selected from the group consisting of protein catabolic process, regulation of autophagy, regulation of endopeptidase activity, and regulation of proteolysis;
    treating skin with a putative agent; conducting a transcriptional assessment of the eigengene in the treated skin; and identifying the putative agent as an effective clean and detox agent if the eigengene is up-regulated in the treated skin.

2. The method of claim 1, further comprising deriving a second eigengene for a co-expression module determined from a set of genes transcriptionally up-regulated in human skin exhibiting the desirable cosmetic phenotype and a set of genes associated with a cell repair and rebuild biological theme selected from the group consisting of amino sugar biosynthetic process, cell adhesion junction, deoxyribonucleic acid repair, glycerolipid metabolic process, response to growth factor stimulus, ribonucleic acid processing, and Wnt receptor signaling pathway; treating skin with the putative agent;
    conducting a transcriptional assessment of the second eigengene in the treated skin;
    and identifying the putative agent as an effective cell repair and rebuilding agent if the second eigengene is up-regulated in the treated skin.

* * * * *